United States Patent [19]

Hirayama et al.

[11] Patent Number: 5,338,418
[45] Date of Patent: Aug. 16, 1994

[54] PROCESS FOR PRODUCTION OF HYDROXOCOBALAMIN

[75] Inventors: Takayuki Hirayama; Takashi Kiyota, both of Yokohama, Japan

[73] Assignee: Nippon Oil Co., Ltd., Tokyo, Japan

[21] Appl. No.: 944,463

[22] Filed: Sep. 14, 1992

[30] Foreign Application Priority Data

Sep. 17, 1991 [JP] Japan .................. 3-236486

[51] Int. Cl.$^5$ .................. C07H 23/00; C07D 403/14
[52] U.S. Cl. .................. 204/158.21; 536/26.41; 536/26.42; 536/26.43; 204/157.64; 204/157.67
[58] Field of Search ............... 536/26.43, 26.42, 26.41; 204/158.21

[56] References Cited

U.S. PATENT DOCUMENTS

| | | | |
|---|---|---|---|
| 2,626,888 | 1/1953 | Kutosh et al. | 536/26.43 |
| 2,668,137 | 2/1954 | Briggs et al. | 536/26.43 |
| 2,694,679 | 11/1954 | Holland et al. | 536/26.43 |
| 2,695,862 | 11/1954 | Rickes et al. | 536/26.43 |
| 2,830,009 | 4/1958 | Ziegler | 536/26.43 |
| 3,448,099 | 6/1969 | Boige | 260/211.7 |
| 4,383,110 | 5/1983 | Kinoshita et al. | 536/26.43 |

FOREIGN PATENT DOCUMENTS

| | | | |
|---|---|---|---|
| 0689028 | 6/1964 | Canada . | |
| 109859 | 5/1984 | European Pat. Off. | C12P 19/42 |
| 1670193 | 7/1970 | Fed. Rep. of Germany . | |
| 1325304 | 3/1963 | France . | |
| 1330307 | 5/1963 | France . | |
| 2309564 | 11/1976 | France | C07H 23/00 |
| 1012360 | 12/1965 | United Kingdom . | |
| 2088383 | 6/1982 | United Kingdom | C07H 23/00 |

OTHER PUBLICATIONS

Tetsuo Toraya, "Vitamin B12 and Related Compounds", *Vitamin Science* II:493–494, 1980 (partial translation enclosed).

*Primary Examiner*—Johnnie R. Brown
*Assistant Examiner*—Gary L. Kunz
*Attorney, Agent, or Firm*—Seed and Berry

[57] ABSTRACT

A process for the production of hydroxocobalamin that eliminates cyanocobalamin as an intermediate. Coenzyme-type vitamin $B_{12}$ is first absorbed to a divinylbenzene/styrene resin which is washed with warm water and then eluted with a solution containing at least 25% of a lower alcohol. The eluate is then irradiated with a light that causes the conversion of coenzyme-type vitamin $B_{12}$ to hydroxocobalamin. Finally, the solution of hydroxocobalamin is treated with alumina or silica which binds the impurities leaving behind the highly purified hydroxocobalamin in the flow-through.

1 Claim, No Drawings

PROCESS FOR PRODUCTION OF HYDROXOCOBALAMIN

BACKGROUND OF THE INVENTION

1. Field of the Invention

The present invention relates to a novel process for production of hydroxocobalamin.

2. Related Art

Various cobalamin—series compounds including hydroxocobalamin are mainly derived from Co-enzyme type vitamin $B_{12}$ produced by fermentation. It is known in the art that the Co-enzyme type vitamin $B_{12}$ is optically converted to hydroxocobalamin (see, vitamin Science (II) Water Soluble Vitamin, P 493, Tokyo Kagaku Dojin).

It has been believed, however, that direct isolation and purification of hydroxocobalamin from Co-enzyme type vitamin $B_{12}$, which is present in a very low concentration among various impurities is very difficult, because hydroxocobalamin is highly reactive and unstable. For example, Japanese Examined Patent Publication (Kokoku) No. 39-18148 (GB 1012360) describes "the case wherein hydroxocobalamin is directly produced from a fermentation broth is very difficult because hydroxocobalamin is highly reactive and hydroxocobalamin easily binds to other ions present in a solution ...", and this is generally recognized in the art.

Therefore, hydroxocobalamin is obtained from Co-enzyme type vitamin $B_{12}$ produced by fermentation by a process comprising the steps of conversion of Co-enzyme type vitamin $B_{12}$ to stable cyanocobalamin, purification of the cyanocobalamin, and conversion of the purified cyanocobalamin to hydroxocobalamin (see, Japanese Examined Patent Publication No. 39-18148, and Japanese Examined Patent Publication No. 46-14664 (U.S. Pat. No. 3448099)).

However, the process wherein hydroxocobalamin is obtained from coenzyme-type vitamin $B_{12}$ going through cyanocobalamin as an intermediate is not advantageous with respect to yield, production costs, and the like. Such a process requires numerous, complex steps. In particular, coenzyme-type vitamin $B_{12}$ is first converted to cyanocobalamin; the cyanocobalamin is isolated and purified in a sub-process requiring several steps; the purified cyanocobalamin is converted to hydroxocobalamin; and, finally, the hydroxocobalamin is isolated and purified.

SUMMARY OF THE INVENTION

The present invention provides a very simple process comprising a small number of steps for isolating and purifying hydroxocobalamin from coenzyme-type vitamin $B_{12}$ produced by fermentation. The inventive process comprises a particular combination of a few steps, including an optical conversion step of coenzyme-type vitamin $B_{12}$ to hydroxocobalamin. Such a process has been believed to be impossible in the art.

Thus, the present invention relates to a process for the production of hydroxocobalamin comprising the steps of:

(1) putting a solution containing Co-enzyme type vitamin $B_{12}$ into contact with a divinylbenzene/styrene copolymer resin so that the Co-enzyme type vitamin $B_{12}$ is adsorbed in the resin;

(2) washing the resin with purified water or aqueous washing solution at a temperature between 30° C. and 70° C. so as to remove impurities;

(3) extracting the Co-enzyme type vitamin $B_{12}$ adsorbed on the resin with an aqueous solution containing at least 25% by of a lower alcohol, to obtain an eluate containing Co-enzyme type vitamin $B_{12}$;

(4) irradiating the eluate with light to convert Co-enzyme type vitamin $B_{12}$ to hydroxocobalamin; and (5) treating the hydroxocobalamin-containing solution from step (4) with an inorganic adsorbent and recovering hydroxocobalamin.

DETAILED DESCRIPTION

A solution containing Co-enzyme type vitamin $B_{12}$ used as a starting material of the present process is obtained by fermentation using a vitamin $B_{12}$-producing microorganism. The vitamin $B_{12}$-producing microorganisms include, but are not limited to, those belonging to the genus Propionibacterium, Streptomyces, Arthrobecter, Corinebacterium, Rhodopseudomonas, Mycobacterium, Pseudomonas, or the like.

A solution containing Co-enzyme type vitamin $B_{12}$ is, for example, a culture supernatant or filtrate obtained by eliminating microbial cells from a fermentation broth obtained by aerobically or unaerobically culturing said producer microorganism; an extract obtained by extracting microbial cells of the producer microorganism with an extracting agent such as water or an aqueous extracting agent; a solution obtained by disrupting microbial cells of the producer microorganism with a conventional means such as a mechanical means or ultrasonication, or the like. According to the present invention, it is preferable that an extract be obtained by culturing a vitamin $B_{12}$-producing microorganism, separating the cultured cells in a conventional means, and optionally washing the cells with purified water such as water purified with an ion exchanger, and extracting the cells with purified water such as water purified with an ion exchanger at an elevated temperature, preferably at 60° C. to 95° C. for example, 80° C.

Next, the Co-enzyme type vitamin $B_{12}$-containing solution thus obtained is contacted with a divinylbenzene/styrene type copolymer resin so that the Co-enzyme type vitamin $B_{12}$ is adsorbed on the resin.

The divinylbenzene/styrene type copolymer resin is a copolymer resin obtained from divinylbenzene, styrene or functional derivative thereof as main monomer components, or a copolymer resin derived from divinylbenzene, styrene or functional derivative thereof as main components, and incorporating an aromatic polycarboxylate unsaturated alkyl ester represented by the formula:

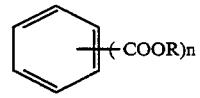

wherein R is an unsaturated $C_8$–$C_{10}$ alkyl having a carbon-carbon double band, and n being 2 or 3. This resin is sometimes abbreviated as a DST resin.

These resins are generally obtained by copolymerizing the above-mentioned monomers with a known radical initiator. Preferably, styrene or a functional derivative thereof comprises 30 to 80%, preferably 45 to 70% by weight of the resin and the aromatic polycarboxylate/unsaturated alkyl ester comprises, if any, 0.1 to 30% by weight preferably 1 to 10% by weight of the resin.

Particular DST resins include, for example, AMBERLITE XAD-2®, XAD-4® and 2000®, DIAION HP20®, SEPABEADS SP207® and SP825®.

According to the present process, contacting the Co-enzyme type vitamin $B_{12}$ with the resin adsorbent can be carried out using any means that ensures sufficient contact thereof.

For example, a batch system wherein the Co-enzyme type vitamin $B_{12}$-containing solution is mixed with the resin adsorbent and optionally the mixture is agitated to ensure sufficient contact, or a column chromatography system wherein an appropriate column is filled with the resin adsorbent and the Co-enzyme type vitamin $B_{12}$-containing solution is passed through the column.

In the case of the batch system, the Co-enzyme type vitamin $B_{12}$-containing solution is adjusted to a suitable pH value, for example a pH value of about 5 to 8, preferably a pH value of about 7, and to the solution is added a suitable amount of the resin adsorbent, for example about 1 to 50% by volume of the resin adsorbent, and the mixture is gently agitated for about 10 minutes to 2 hours, usually about 20 minutes to an hour.

The temperature during the adsorption is preferably lower than room temperature although room temperature may be used. For example, the temperature during adsorption may be between about 10° C. and 30° C.

The column chromatography system for the adsorption can be carried out by passing the Co-enzyme type vitamin $B_{12}$-containing solution through a column filled with a resin adsorbent under the same pH and temperature conditions as for the batch system described above.

According to the present invention, the resin on which Co-enzyme type vitamin $B_{12}$ has been adsorbed is washed with a washing agent to remove impurities and maintain the Co-enzyme type vitamin $B_{12}$ adsorbed on the resin. The impurities to be removed include those derived from the culture broth, for example, salts of aliphatic carboxylic acids such as sodium propionate, sodium burylate and sodium pentanoate, amino acids such as glutamic acid, aspartic acids, proline, leucine, alanine, sugars such as glucose, fructose, ribose and galactose, as well as bases comprising nucleic acids, such as adenine, guanine, cytosine, thymidine and uracil, and the like. The washing increases the purity of Co-enzyme type vitamin $B_{12}$ eluted from the resin adsorbent in a subsequent elution step.

The washing agent is preferably purified water. The purified water is, for example, water purified by an ion exchanger and having a specific resistance of $100 \times 10^4$ ohm.cm, prepared by passing water through a column filled with an ion exchange resin, such as Amberlite IR-120$^B$ and Amberlite IRA-410. The purified water is used to wash the resin absorbent at a temperature between 30° C. and 70° C., preferably between about 45° C. and 55° C. Alternatively, the washing agent may be an aqueous solution of an acid such as acetic acid, phosphoric acid, sulfuric acid, boric acid, hydrochloric acid or the like, having a concentration of 0.1 to 1.0% by weight, at a temperature between 30° C. and 70° C., preferably between about 45° C. and 55° C. Moreover, an aqueous solution of a lower alcohol having a low concentration, for example a methanol, ethanol or isopropanol aqueous solution having a concentration of 5 to 20%, such an 20% aqueous methanol, 10% aqueous ethanol, 5% aqueous isopropanol or the like, may be used for the washing. The washing agent may be selected depending on the nature and amount of the impurities, the kind of the resin adsorbent, and the like.

According to the present invention, the Co-enzyme type vitamin $B_{12}$ adsorbed on the washed resin was eluted with an eluting agent so as to obtain an active fraction containing Co-enzyme type vitamin $B_{12}$ but not containing impurities.

As the eluting agent, any agent that desorbs and elutes the Co-enzyme type vitamin $B_{12}$ from the resin adsorbent, and does not interfere with irradiation with light in a subsequent conversion step. The eluting agent may be an aqueous solution of a lower alcohol such as methanol, ethanol or isopropanol, or a mixture thereof, having a concentration of at least 25%. Preferably, the eluting agent is an aqueous solution of methanol having a concentration of 25 to 90%, most preferably 50%. The elution can be carried out at room temperature although an elevated or lowered temperature may be used if desired. For example, an elution temperature is between about 20° C. and 60° C.

Since the eluate thus obtained contains Co-enzyme type vitamin $B_{12}$ in a substantially purified form, the Co-enzyme type vitamin $B_{12}$ can be converted to hydroxocobalamin by irradiation of light. The light for irradiation is ultraviolet or visible light, for example, having a wave length of 300 to 800 nm. As a source of the light having such a wave length, a high pressure mercury arc lamp, a fluorescent lamp or the like can be used. The irradiation is continued until the disappearance of Co-enzyme type vitamin $B_{12}$ is confirmed by spectroscopy, high performance liquid chromatography or the like. For example, the irradiation is carried out with a 400 W high pressure mercury arc lamp for 20 to 40 minutes. Other conditions for the irradiation, such as the concentration of Co-enzyme type vitamin $B_{12}$ in a reaction medium, the kind of medium, temperature, etc. are not critical. The concentration of Co-enzyme type vitamin $B_{12}$ in a medium to be irradiated is preferably up to 50 mM, more preferably 0.1 to 10 mM. The kind of medium is conveniently the same as that used in the preceding step. The temperature is preferably 5° C. to 30° C.

Since hydroxocobalamin in a solution thus obtained is highly reactive and unstable, it cannot be subjected to a lot of purification steps. Therefore, according to the present invention, immediately after the irradiation, the irradiated hydroxocobalamin solution is put into contact with an inorganic adsorbent to remove impurities such as those present prior to the irradiation and those generated by the irradiation such as adenosine-5'-aldehyde.

As the inorganic adsorbent, silica gel, alumina or the like may be used, with alumina being preferable. The adsorption is preferably carried out by passing an irradiated solution through a column filled with the inorganic adsorbent and recovering a flow-through fraction. Alternatively, in a batch process, an irradiated solution may be added to the inorganic adsorbent, and after mixing the mixture the adsorbent is removed by a conventional procedure such as filtration, centrifugation or the like so as to recover a purified hydroxocobalamin solution.

The treated solution is concentrated for hydroxocobalamin according to a conventional procedure such as evaporation under reduced pressure, membrane separation or the like, and hydroxocobalamin crystallized so as to recover hydroxocobalamin. For example, the concentrated solution of hydroxocobalamin is adjusted to a pH value of about 4.0, and acetone is added to the pH adjusted solution so as to crystallize hydroxocobalamin, which is then recovered at a purity of at least 95%.

EXAMPLES

Next, the present invention is further explained by Example, but is not limited to the said Example.

480 liters of a culture broth containing 25 mg/l of Co-enzyme type vitamin $B_{12}$, obtained by fermentation using a Co-enzyme type vitamin $B_{12}$ producing microorganism, *Propionibacteriom Shermanii* IFO12391, was centrifuged to recover the cells. The cells were thoroughly washed with purified water and extracted with 400 liters of water at 80° C. to obtain 400 liters of an extract containing crude Co-enzyme type vitamin $B_{12}$. The extract was passed through a column filled with 6 liters of a divinylbenzene/styrene type copolymer resin, AMBERLITE XAD2000®, so that Co-enzymetype vitamin $B_{12}$ is adsorbed on the resin. 250 liters of water purified by ion exchanger were continuously passed through the column at a temperature of 60° C. so as to wash out the impurities. Next, Co-enzyme type vitamin $B_{12}$ was eluted with 28 liters of a 50% aqueous methanol.

The eluate was irradiated with a 400 W high pressure mercury arc lamp for 20 minutes to convert Co-enzyme type vitamin $B_{12}$ to hydroxocobalamin. The irradiated eluate was passed through a column filled with 750 ml of alumina, to recover a flow-through fraction, which was then concentrated to 750 ml under reduced pressure.

The concentrate was adjusted to a pH value of 4.0 with acetic acid, and 3.9 liters of acetone were added to the pH-adjusted concentrate, which was then allowed to stand at 5° C. for 24 hours so as to crystallize the hydroxocobalamin. 3.7 g of hydroxocobalamin were obtained at a purity of at least 95%.

According to the present invention, high purity hydroxocobalamin can be obtained by a small number of steps from a culture broth containing Co-enzyme type vitamin $B_{12}$ without going through cyanocobalamin as an intermediate.

We claim:
1. A process for the production of hydroxocobalamin comprising:
    (1) contacting a solution containing coenzyme-type vitamin $B_{12}$ with a divinylbenzene/styrene copolymer resin so that the coenzyme-type vitamin B is absorbed onto the resin;
    (2) washing the resin with purified water or aqueous washing solution at a temperature between 30° C. and 70° C. so as to remove the impurities;
    (3) eluting the coenzyme-type vitamin $B_{12}$ absorbed on the resin with an aqueous solution containing at least 25% by volume of a lower alcohol;
    (4) irradiating the eluate with light so as to convert coenzyme-type vitamin $B_{12}$ to hydroxocobalamin;
    (5) contacting the hydroxocobalamin-containing solution from step (4) with silica or alumina; and
    (6) recovering the unbound, purified hydroxocobalamin.

* * * * *